United States Patent
Ochoa

(10) Patent No.: US 10,035,083 B2
(45) Date of Patent: Jul. 31, 2018

(54) MUD PUMP AND VACUUM GAS EXTRACTION SYSTEM

(71) Applicant: Baker Hughes Incorporated, Houston, TX (US)

(72) Inventor: Brian Ochoa, Hannover (DE)

(73) Assignee: BAKER HUGHES, A GE COMPANY, LLC

( * ) Notice: Subject to any disclaimer, the term of this patent is extended or adjusted under 35 U.S.C. 154(b) by 98 days.

(21) Appl. No.: 15/067,361

(22) Filed: Mar. 11, 2016

(65) Prior Publication Data
US 2017/0259192 A1    Sep. 14, 2017

(51) Int. Cl.
| | | |
|---|---|---|
| B01D 19/00 | (2006.01) | |
| F04B 19/22 | (2006.01) | |
| F04B 49/22 | (2006.01) | |
| F04C 2/22 | (2006.01) | |
| F04C 14/24 | (2006.01) | |
| F04B 19/06 | (2006.01) | |
| E21B 21/06 | (2006.01) | |
| E21B 21/10 | (2006.01) | |
| E21B 49/08 | (2006.01) | |
| H01J 49/26 | (2006.01) | |
| G01N 30/20 | (2006.01) | |
| G01N 30/72 | (2006.01) | |

(52) U.S. Cl.
CPC ........ *B01D 19/0052* (2013.01); *E21B 21/067* (2013.01); *E21B 21/106* (2013.01); *E21B 49/086* (2013.01); *F04B 19/06* (2013.01); *F04B 19/22* (2013.01); *F04B 49/22* (2013.01); *F04C 2/22* (2013.01); *F04C 14/24* (2013.01); *F04C 2210/22* (2013.01); *F04C 2220/20* (2013.01); *G01N 30/20* (2013.01); *G01N 30/7206* (2013.01); *H01J 49/26* (2013.01)

(58) Field of Classification Search
CPC .... B01D 19/00–19/0495; E21B 49/086; E21B 21/06–21/07; F04B 19/06; F04B 19/12; F04C 2/22; F04C 14/24; F04C 2210/22; F04C 2220/20; G01N 30/20; G01N 30/7206; H01J 49/26
See application file for complete search history.

(56) References Cited

U.S. PATENT DOCUMENTS

| | | | | |
|---|---|---|---|---|
| 2,376,221 | A * | 5/1945 | Baker ................ | B01D 19/0078 366/118 |
| 3,895,927 | A * | 7/1975 | Bournham, Sr. .. | B01D 19/0021 96/163 |
| 3,975,171 | A * | 8/1976 | Burnham, Sr. .... | B01D 19/0052 366/262 |
| 4,294,593 | A * | 10/1981 | Rehm ................ | B01D 19/0057 96/160 |
| 4,700,872 | A * | 10/1987 | Keyes ...................... | A61O 5/40 222/162 |
| 2004/0265176 | A1* | 12/2004 | Kerherve ........... | B01D 19/0005 422/68.1 |
| 2012/0000279 | A1 | 1/2012 | Daniel et al. | |
| 2015/0198039 | A1* | 7/2015 | Marshall ............... | E21B 49/086 73/152.42 |

FOREIGN PATENT DOCUMENTS

WO    2010/059601 A2    5/2010

* cited by examiner

*Primary Examiner* — T. Bennett McKenzie
(74) *Attorney, Agent, or Firm* — Shawn Hunter

(57) ABSTRACT

Systems and methods for extracting hydrocarbon gas utilize a vacuum chamber with a mud chamber portion that is expandable and contractible. Gas is extracted at vacuum pressures.

11 Claims, 4 Drawing Sheets

MUD PUMP AND VACUUM GAS EXTRACTION SYSTEM

BACKGROUND OF THE INVENTION

1. Field of the Invention

The invention relates generally to systems and methods used to flow drilling muds and to extract gas from such muds.

2. Description of the Related Art

A standard drilling process includes circulating drilling mud through a well to establish well control, cutting removal and bit cooling. When drilling through a medium containing gas, condensate or oil, the hydrocarbons are released from the penetrated interval. The released gas is then transported to the surface in the drilling mud. Additional gas may be released into the mud from the oil or condensate due to changing conditions from subsurface to surface. The amount of released gas, not bound or trapped in or on the cuttings, depends on the porosity, permeability and hydrocarbon saturation of the formation.

Mud logging is a commonly applied service in the hydrocarbon production industry and relates to extraction and measurement of hydrocarbons which are present in the drilling mud. Measurements are conducted at the surface during drilling operations with a mass spectrometer, a gas chromatograph, or a combination of both. Of particular relevance to the industry are the hydrocarbons which are released from the penetrated lithological units and recorded at the surface once they become evaporated into gaseous phase under atmospheric conditions. Ideally, the measured hydrocarbons are only from the milled formation and can, therefore, provide highly valuable information when correlated with the corresponding depth and corrected for artifacts like recycled connection and/or tripping gas.

Depending upon the mud and hydrocarbon combination, the amount of each hydrocarbon in solution or present in gas phase may vary. Conventional hydrocarbon extraction (C1 to C8) is accomplished by feeding mud through a vessel with a mechanical agitator and sucking the evaporated hydrocarbons from the headspace of the device (gas trap) towards the measuring unit. Based upon the measured hydrocarbon compositions and the fluid type used for the drilling operation (water-based mud, oil-based mud and synthetic oil-based mud) features like gas/oil contacts and oil/water contacts can be determined.

SUMMARY OF THE INVENTION

The present invention provides systems and methods for extracting hydrocarbon gas from drilling mud. The described systems and methods utilize a degassing device with a degassing chamber. The degassing chamber has at least one mud chamber portion into which mud is flowed and which is expandable and contractible.

A first embodiment for a mud pump and extraction system is described which includes a degassing chamber with a mud chamber portion. A degassing member in the form of a piston is axially moveable within the degassing chamber to expand or contract the mud chamber portion of the degassing chamber. Mud within the mud chamber portion will have gas extracted from it when the mud chamber portion is expanded. In a described embodiment, the degassing chamber is operably associated with a supply of hydrocarbon-bearing drilling mud as well as a mud collection sump to which degassed mud is flowed. Also in a described embodiment, the degassing device is operably associated with a gas collection trap to which extracted gas is flowed following extraction. The gas collection trap is associated with a gas analysis device which preferably includes a gas chromatograph and/or a mass spectrometer. A preferred method of transmitting extracted gas from the vacuum chamber to the gas collection trap is to flow the extracted gas into a gas sample line which uses a suction flow of air to transport the extracted gas.

An alternate embodiment is also described wherein the mud pump and extraction system includes a degassing device in the form of a rotary extractor. A degassing member in the form of a rotor is movable in rotary fashion within a degassing chamber. As the rotor rotates, a mud chamber portion of the degassing chamber is expanded to extract gas from drilling mud.

In exemplary operation of mud pump and gas extraction systems in accordance with the present invention, hydrocarbon-bearing mud flows into a degassing chamber in a degassing device. The mud chamber portion of the degassing chamber is then expanded to extract gas from the mud. The mud chamber portion is then contracted as extracted gas is removed from the mud chamber portion via a gas suction valve. Degassed mud is flowed to the mud collection sump. Extracted gas is directed from the degassing chamber to the gas collection trap and is subsequently analyzed by a gas analysis device.

BRIEF DESCRIPTION OF THE DRAWINGS

For a thorough understanding of the present invention, reference is made to the following detailed description of the preferred embodiments, taken in conjunction with the accompanying drawings, wherein like reference numerals designate like or similar elements throughout the several figures of the drawings and wherein.

DETAILED DESCRIPTION OF THE PREFERRED EMBODIMENTS

Figure 1:
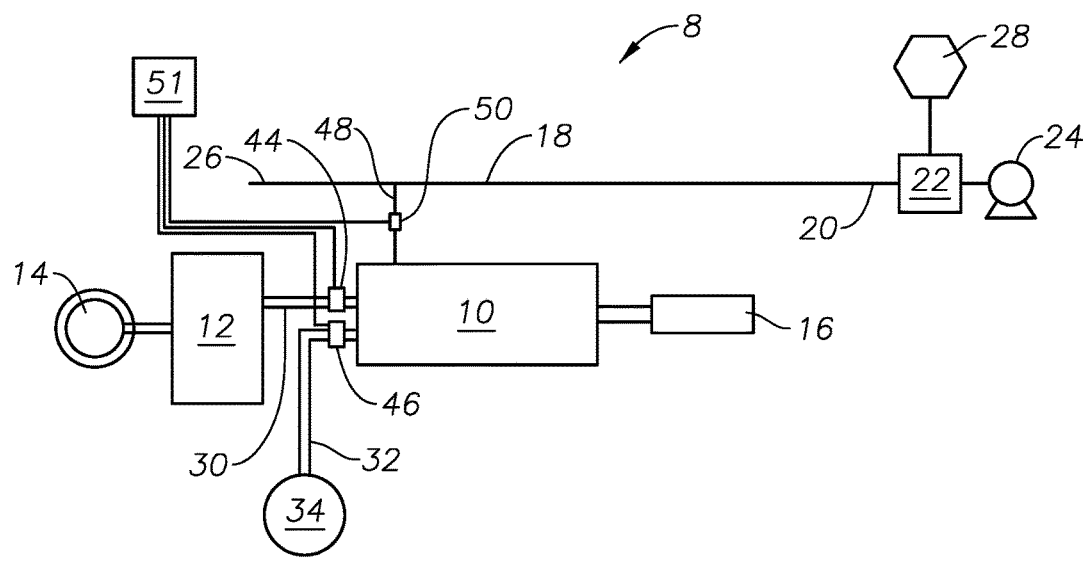
FIG. 1 is a schematic plan view of a wellbore with an associated mud pump and gas extraction device and other components in accordance with the present invention.

FIGS. 1-5 is a schematic plan view which illustrates an exemplary mud pump and gas extraction system 8 which includes a degassing device 10 in accordance with the present invention. As FIG. 1 depicts, the degassing device 10 is typically located proximate a supply 12 of drilling mud which has been returned up the annulus of associated wellbore 14. It is noted, however, that the invention is not limited to use with drilling mud that is returned from a wellbore annulus. Rather, any drilling mud, including mud that is to be pumped into a wellbore might also be used. The drilling mud within the supply 12 contains hydrocarbon gas which is to be extracted. A reciprocating device 16 is located proximate the mud pump and extraction device 10 and is used to actuate a piston within the degassing device 10, as will be described. A gas sample line 18 is also located proximate the degassing device 10. At the downstream end 20 of the gas sample line 18 is a gas collection trap 22. A vacuum pump 24 is operably associated with the gas sample line 18 at its downstream end 20 so as to draw air through the gas sample line 18 from the upstream end 26 toward the downstream end 20 and the gas collection trap 22. A gas analysis device 28 is operably associated with the gas collection trap 22 in order to analyze properties of gas collected within the gas collection trap 22. In preferred embodiments, the gas analysis device 28 includes a gas chromatograph and/or a mass spectrometer.

Now also referring to FIGS. 2-5, it can be seen that a first mud conduit 30 transmits mud from the drilling mud supply 12 to the degassing device 10. A second mud conduit 32 extends from the degassing device 10 to a mud collection sump 34. As best shown in FIGS. 2-5, the exemplary degassing device 10 includes an outer housing 36 which defines a degassing chamber 38 within. A piston 40 and shaft 42 are retained within the degassing chamber 38 and are reciprocally moveable within. The piston 40 serves as a degassing member which will extract, gas from the drilling mud via axial movement within the degassing chamber 38. The shaft 42 and piston 40 are moved axially within the degassing chamber 38 by the reciprocating motor 16 which operates to generate suction and discharge strokes.

The outer housing 36 is provided with a mud inlet valve 44 and a mud outlet valve 46. Preferably, both the mud inlet valve 44 and mud outlet valve 46 are one-way valves. The mud inlet valve 44 only permits mud to flow into the degassing chamber 38 when open. The mud outlet valve 46 only permits mud to flow out of the degassing chamber 38.

A gas sample conduit 48 is located outside of the outer housing 36 and allows fluid transmission between the degassing chamber 38 and the gas sample line 18. The gas sample conduit 48 is preferably under vacuum or at least at a pressure lower than that of the degassing chamber 38 so that gas will flow out of the degassing chamber 38. A gas suction valve 50 is located between the degassing chamber 38 and the gas sample conduit 48. The gas suction valve 50 is preferably a one-way valve such that, when the gas suction valve 50 is open, fluid will flow from the degassing chamber 38 to the gas sample conduit 48.

The mud inlet valve 44, mud outlet valve 46 and gas suction valve 50 are operably interconnected with a controller 51 which governs the opening and closing of these valves as described herein in coordination with the strokes of the reciprocating motor 16. The controller 51 may comprise a programmable digital computer with suitable programming for carrying out the general valve control steps described herein.

Figure 2:
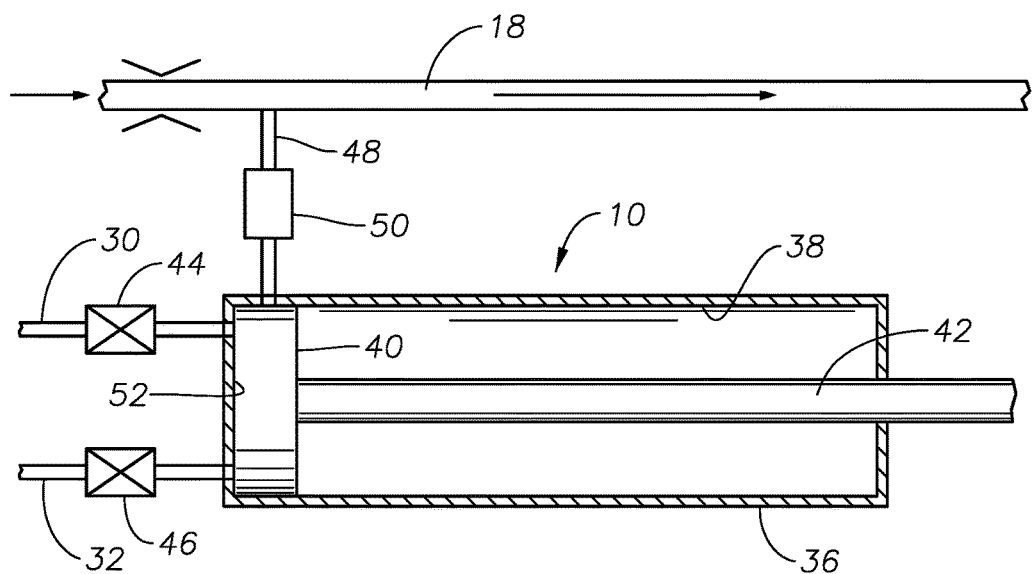
FIG. 2 is a side, cross-sectional view of an exemplary mud pump and gas extraction device in accordance with the present invention.
Figure 3:
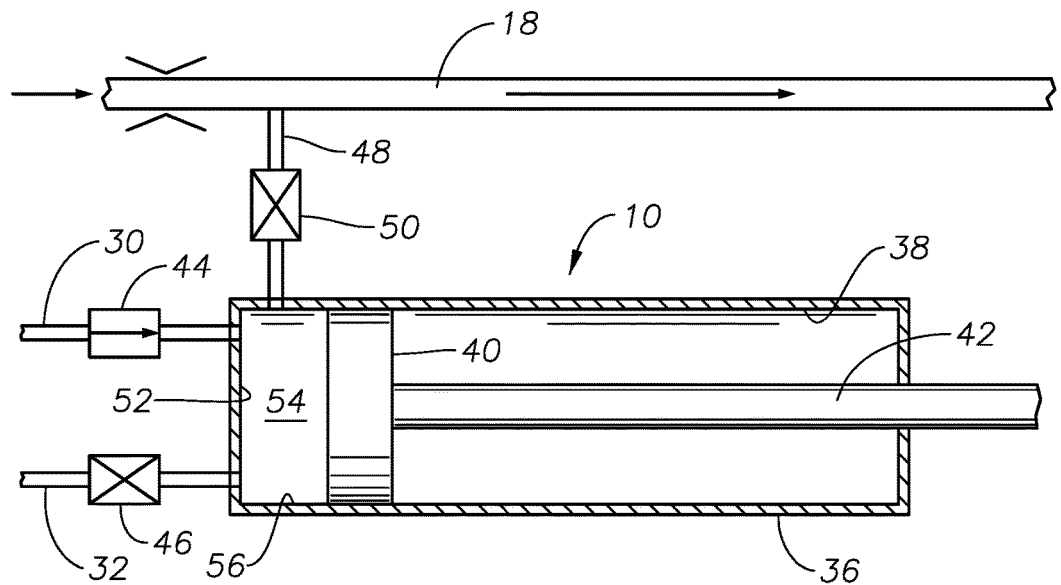
FIG. 3 is a side, cross-sectional view of the mud pump and gas extraction device of FIG. 2, during a mud suction stroke.
Figure 4:
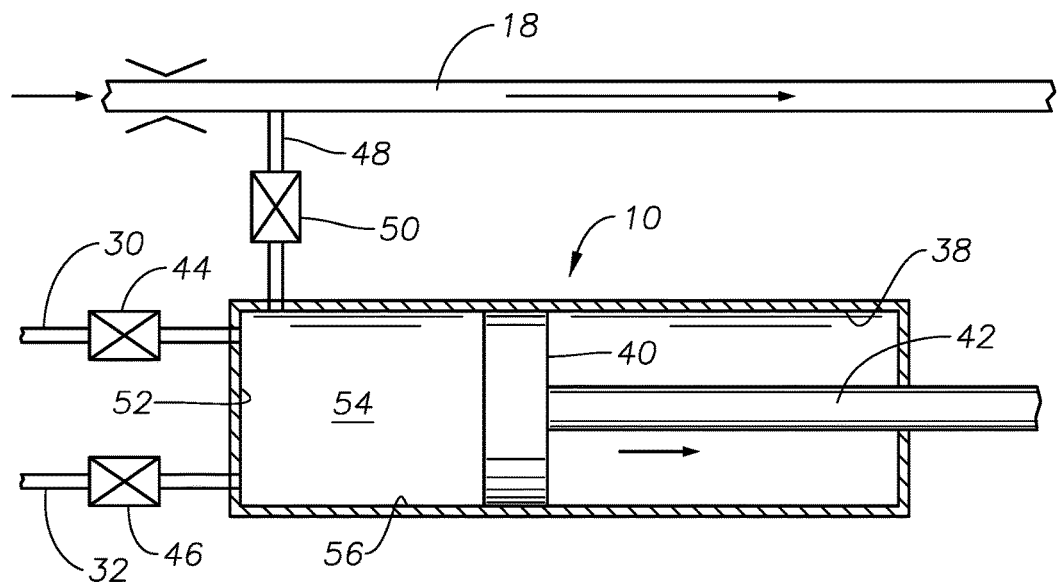
FIG. 4 is a side, cross-sectional view of the mud pump and gas extraction device of FIGS. 2-3, now during a mud gas extraction stroke.

FIG. 2 shows an initial position for the degassing device 10 wherein the piston 40 is located at the proximal wall 52 of the degassing chamber 38 such that essentially no fluid is located between the piston 40 and the proximal wall 52 of the degassing chamber 38. Mud inflow and mud outflow valves 44 and 46 are closed. In FIG. 3, the piston 40 is moved away from the proximal wall 52. The mud inflow valve 44 opens and mud 54 flows into the mud chamber portion 56 of the degassing chamber 38. Next, the mud pump inflow valve 44 is closed, as depicted in FIG. 4, as the piston 40 is further moved away from the proximal wall 52, thereby increasing the size of the mud chamber portion 56 within which the mud is contained. As this occurs, gas is extracted from the mud 54.

Figure 5:
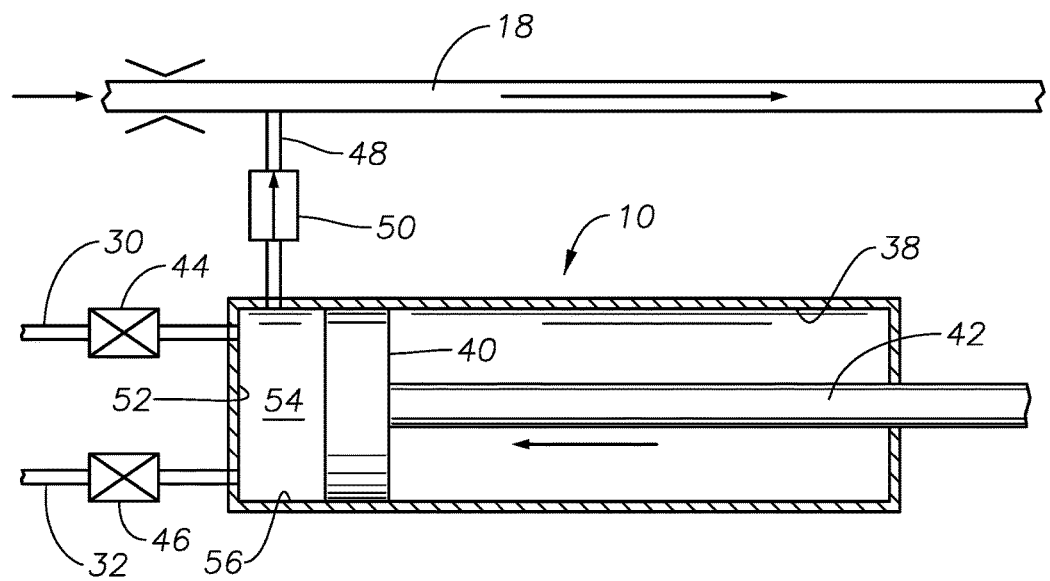
FIG. 5 is a side, cross-sectional view of the mud pump and gas extraction device of FIGS. 2-4, now shown during gas extraction from the pump chamber.
Figure 6:
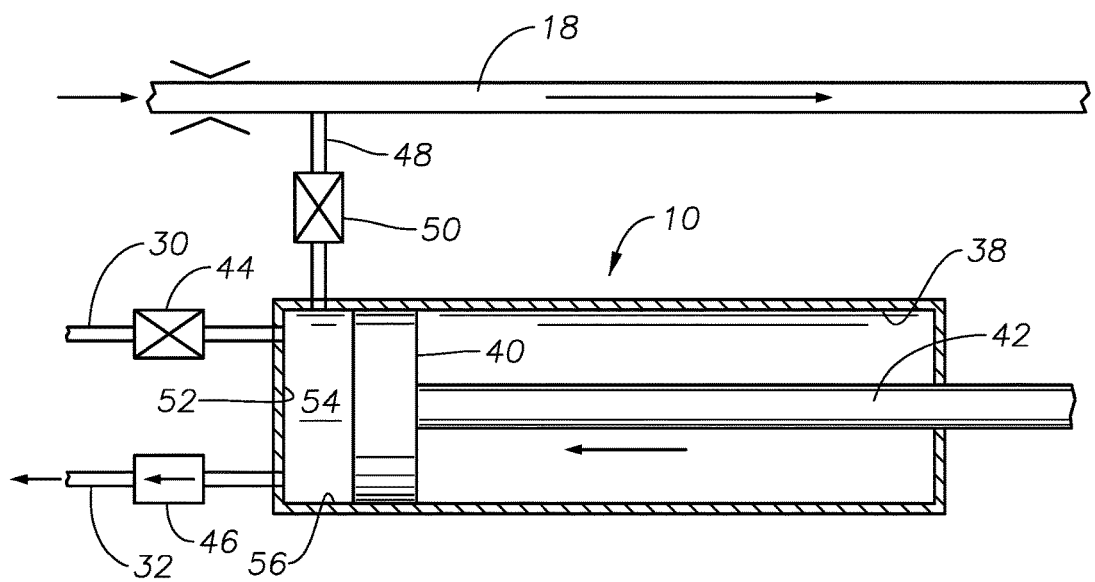
FIG. 6 is a side, cross-sectional view of the mud pump and gas extraction device of FIGS. 2-5, now shown during a mud discharge stroke.

The subsequent step is illustrated in FIG. 5, wherein the gas suction valve 50 is then opened as the piston 40 is moved toward the proximal wall 52 to help evacuate the extracted gas from the mud chamber portion 56. Thereafter, the mud outflow valve 46 is opened (FIG. 6) allowing now degassed mud to flow from the mud chamber portion 56 to the mud collection sump 34.

Hydrocarbon gas which has been extracted from the drilling mud 54 passes through the gas suction valve 50 and gas sample conduit 48 and into the gas sample line 18. Extracted gas is then transported to the gas collection trap 22 via gas sample line 18 under the impetus of suction generated by vacuum pump 24. The extracted gas can then be analyzed by gas analysis device 28.

Figure 7:
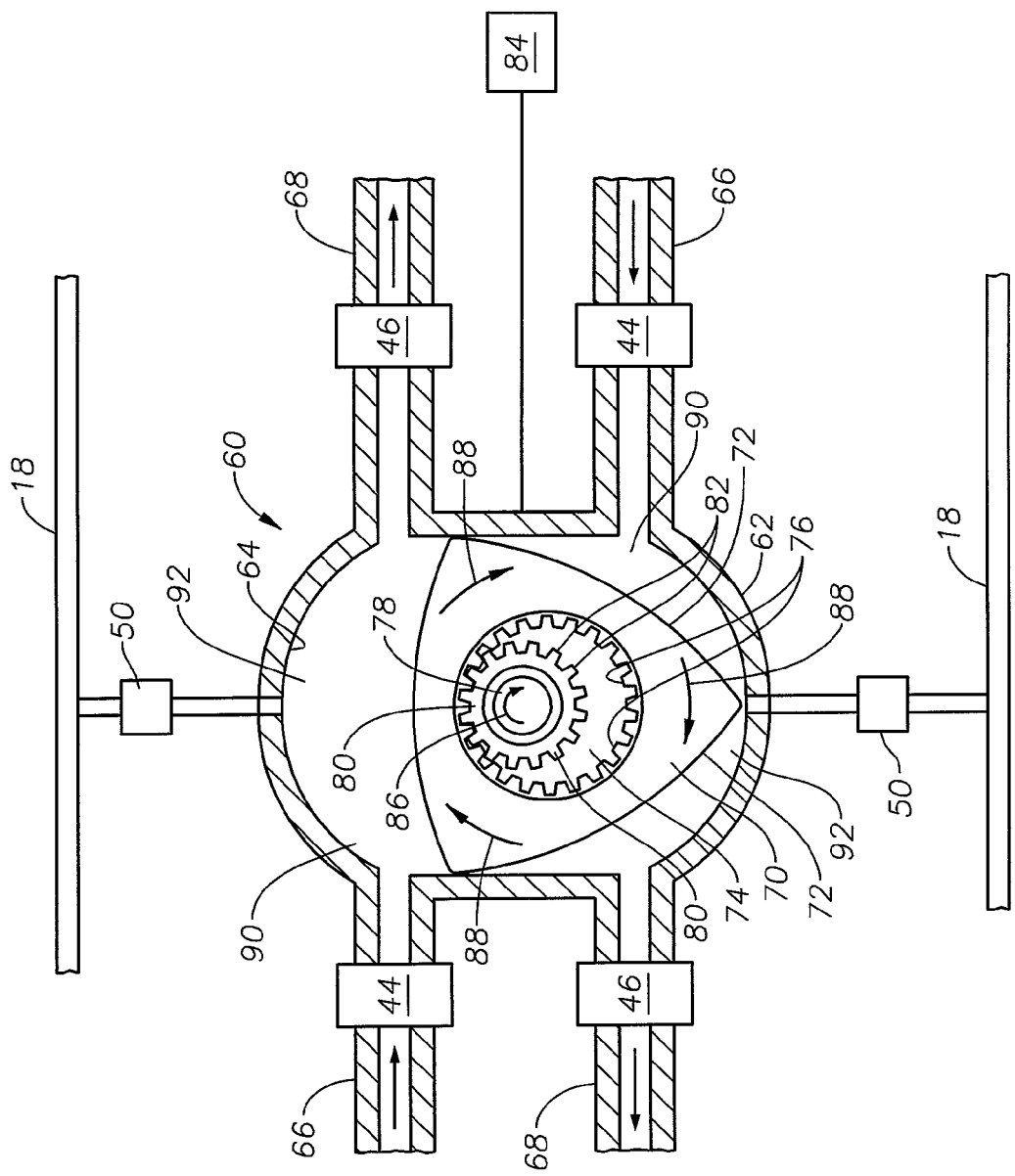
FIG. 7 is a side, cross-sectional view of an alternative embodiment for a mud pump and gas extraction device in accordance with the present invention.

FIG. 7 illustrates an alternative degassing device which can be used in place of degassing device 10 described previously. Except where otherwise noted, the system within which the alternative degassing device operates is the same as the mud pump and extraction system 8 described earlier. The alternative degassing device is a rotary extractor 60 which includes an outer housing 62 which encloses an elliptical degassing chamber 64. Mud inlets 66 and mud outlets 68 allow communication of mud into and out of the degassing chamber 64. In the depicted embodiment, there are two mud inlets 66 and two mud outlets 68, each of which providing communication with separate portions of the degassing chamber 64. Gas sample conduits 48 extend from the degassing chamber 64 to gas sample lines 18. Although two separate gas sample lines 18 are shown, it will be understood that there might be only a single gas sample line 18 into which both gas sample conduits 48 will feed. A gas suction valve 50 is incorporated into each gas sample conduit 48.

A triangular rotor 70 having curved lobes 72 is retained within the degassing chamber 64. The rotor 70 has a central opening 74 lined with gear teeth 76. A rotary shaft 78 is disposed within the central opening 74. The rotary shaft 78 has a gear 80 mounted upon it with teeth 82 which intermesh with gear teeth 76 of the central opening 74. The rotor 70 is rotated in an eccentric, rotational manner within the degassing chamber 64 of the housing 62 in a manner similar to the movement of the rotor of a rotary (Wankel) engine. The rotary shaft 78 is rotated by an external prime mover, shown schematically at 84, in the direction indicated by arrow 86. Due to gear engagement, the rotor 70 will then be rotated eccentrically within the degassing chamber 64 in the direction indicated by arrows 88. Rotation of the rotor 70 causes mud to flow into the chamber 64 via mud inlets 66. It is further pointed out that each of the mud inlets 66 in the described embodiment draws mud from mud supply 12, and each of the mud outlets 68 flows mud leaving the degassing chamber 64 to mud collection sump 34.

As the rotor 70 is rotated, gas is extracted from the drilling mud. The inventor has determined that expansion of fluid within a rotary cycle is effective to remove gas from the drilling mud. Mud is drawn into an intake portion 90 of the degassing chamber 64 via mud inlets 66 during the initial stage of the rotary cycle. Then the inlet valves 44 are closed. Mud is then moved from the intake portion 90 to a mud chamber portion 92 of the degassing chamber 64 as the rotor 70 is rotated and moved within the degassing chamber 64. The mud chamber portions 92 are here expanded in volume during this stage of the cycle. As the mud is expanded, gas is freed from the mud and can be removed via the gas suction valves 50 and gas sample conduits 48. Degassed mud is then compressed by the rotor 70 and exits the degassing chamber 64 via the mud outlets 68 as valves 46 are opened. It is noted that in one full rotation of the rotor 70 there are two reciprocating cycles: one in a mud chamber portion 92 in each half of the degassing chamber 64 (see FIG. 7). Therefore, in a preferred embodiment, there are two mud inlets 66 and two mud outlets 68 as well as two gas sample conduits 48. It should be understood that, while the degassing member of degassing device 10 is the piston 40, the degassing member of the degassing device 60 is the rotor 70.

Those of skill in the art will recognize that numerous modifications and changes may be made to the exemplary designs and embodiments described herein and that the invention is limited only by the claims that follow and any equivalents thereof.

What is claimed is:

1. A mud pump and gas extraction system comprising:
    a degassing device having a degassing chamber defined within an outer housing, the degassing device comprising a rotary extractor and the degassing chamber is elliptically shaped;
    a mud inflow valve through which hydrocarbon-bearing drilling mud is flowed into a mud chamber portion of the degassing chamber;
    a depressurizing member retained within the degassing chamber and moveable therewithin to expand the mud chamber portion of the degassing chamber, the depressurizing member comprising a rotor that is rotated eccentrically within the degassing chamber to expand the mud chamber portion;
    wherein the drilling mud flowed into the degassing chamber is isolated within the degassing chamber by closing the mud inflow valve prior to extraction of hydrocarbon gas from the drilling mud;
    wherein hydrocarbon gas is extracted from the hydrocarbon-bearing drilling mud as the depressurizing member is moved within the degassing chamber; and
    a gas suction valve for removal of extracted hydrocarbon gas from the degassing chamber.

2. The mud pump and gas extraction system of claim 1 further comprising a mud outflow valve for removal of degassed mud from the degassing chamber.

3. The mud pump and gas extraction system of claim 1 further comprising a gas collection trap operably associated with the gas suction valve for collection of extracted hydrocarbon gas.

4. The mud pump and gas extraction system of claim 3 further comprising a gas analysis device which is operably associated with the gas collection trap for analysis of extracted hydrocarbon gas.

5. The mud pump and gas extraction system of claim 4 wherein the gas analysis device further comprises at least one of: a gas chromatograph and a mass spectrometer.

6. The mud pump and gas extraction system of claim 3 further comprising:
    a gas sample line which receives extracted hydrocarbon gas from the degassing chamber, the gas sample line further being in communication with the gas collection trap; and
    a vacuum pump operably associated with the gas sample line to create suction through the gas sample line to transport extracted gas to the gas collection trap.

7. A mud pump and gas extraction system comprising:
    a degassing device having a degassing chamber defined within an outer housing, the degassing device comprising a rotary extractor, and wherein the degassing chamber is elliptically shaped;
    a mud inflow valve through which hydrocarbon-bearing drilling mud is flowed into a mud chamber portion of the degassing chamber;
    a depressurizing member retained within the degassing chamber and moveable therewithin to expand the mud chamber portion of the degassing chamber, the depressurizing member comprising a rotor that is rotated eccentrically within the degassing chamber to expand the mud chamber portion;
    wherein the drilling mud flowed into the degassing chamber is isolated within the degassing chamber by closing the mud inflow valve prior to extraction of hydrocarbon gas from the drilling mud;
    wherein hydrocarbon gas is extracted from the hydrocarbon-bearing drilling mud as the depressurizing member is moved within the degassing chamber; and
    a mud outflow valve for removal of degassed mud from the degassing chamber.

8. The mud pump and gas extraction system of claim 7 further comprising a gas suction valve for removal of extracted hydrocarbon gas from the degassing chamber.

9. The mud pump and gas extraction system of claim 7 further comprising a gas collection trap operably associated with the gas suction valve for collection of extracted hydrocarbon gas.

10. The mud pump and gas extraction device of claim 9 further comprising a gas analysis device which is operably associated with the gas collection trap for analysis of extracted hydrocarbon gas.

11. The mud pump and gas extraction device of claim 10 wherein the gas analysis device further comprises at least one of: a gas chromatograph and a mass spectrometer.

* * * * *